United States Patent [19]
Riley et al.

[11] Patent Number: 5,776,082
[45] Date of Patent: Jul. 7, 1998

[54] METHOD AND APPARATUS FOR MEASUREMENT OF POINTS ON THE HUMAN BODY

[75] Inventors: David R. Riley; Gerald D. Riley, both of Russelville, Ark.

[73] Assignees: Stanley E. Gately; Catherine G. Gately, both of Russellville, Ark.

[21] Appl. No.: 707,816

[22] Filed: Sep. 4, 1996

Related U.S. Application Data

[63] Continuation-in-part of Ser. No. 300,485, Sep. 2, 1994, Pat. No. 5,586,558.
[51] Int. Cl.$^6$ .................................................. A61B 5/10
[52] U.S. Cl. ........................................ 600/594; 600/595
[58] Field of Search ................................ 128/774, 781, 128/782; 33/511, 512

[56] References Cited

U.S. PATENT DOCUMENTS

| | | | |
|---|---|---|---|
| 3,722,103 | 3/1973 | Gregoire | 33/174 D |
| 4,033,329 | 7/1977 | Gregory et al. | 128/25 |
| 4,135,498 | 1/1979 | McGee | 128/25 |
| 4,492,236 | 1/1985 | Pile | 128/781 |
| 4,603,486 | 8/1986 | Moroney et al. | 33/512 |
| 4,760,851 | 8/1988 | Fraser et al. | 128/781 |
| 5,443,079 | 8/1995 | Greenwalt | 128/781 |

FOREIGN PATENT DOCUMENTS 1326244  7/1987  U.S.S.R.

*Primary Examiner*—Max Hindenburg
*Attorney, Agent, or Firm*—Ray F. Cox, Jr.

[57] ABSTRACT

The method and apparatus of the present invention measures degree angle and anthropometric linear measurements of the skeletal structure of the human body. The individual stands in reference to the apparatus with the top of the sternoclavicular joint, or suprasternal notch, as a point of origin. Every individual is measured from the same beginning point. Ten component variables are taken with the measuring unit. These variables allow infield studies of individual workers at a work station or exercise on a resistance training program and/or undergoing medical treatment for biomechanical correction. By measuring bone lengths and degree angles of a human body certain characteristics or trends can be found by this systematic measuring procedure.

5 Claims, 7 Drawing Sheets

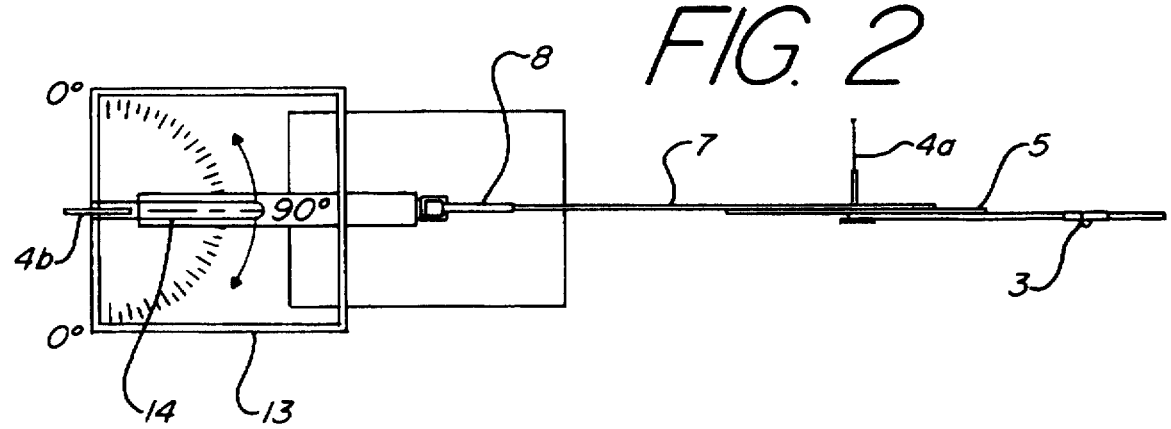
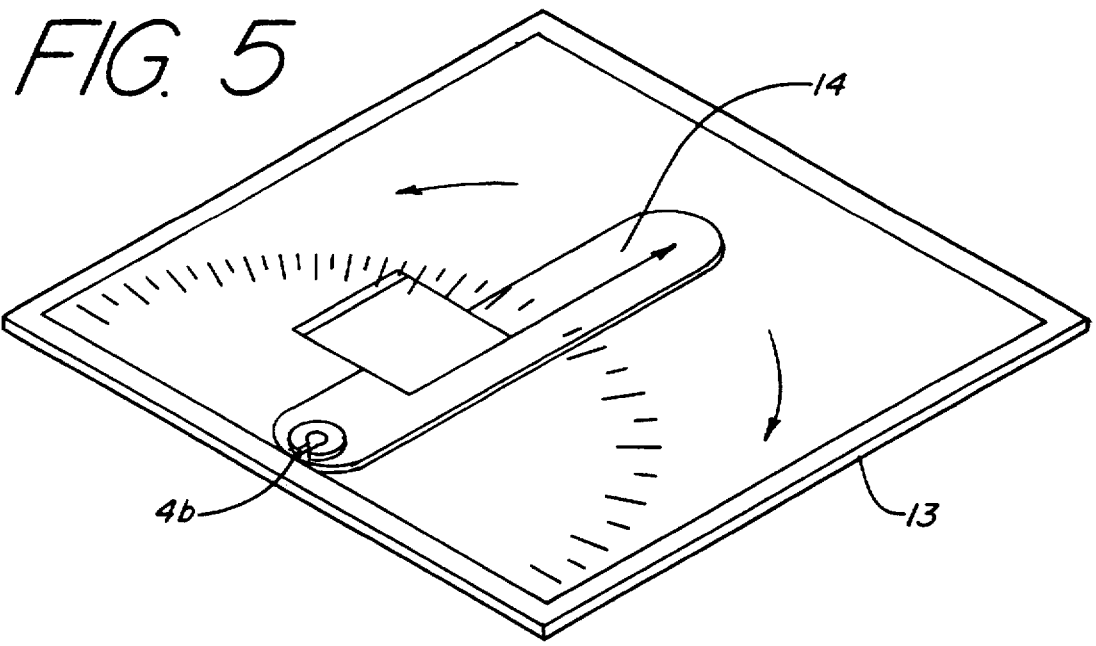

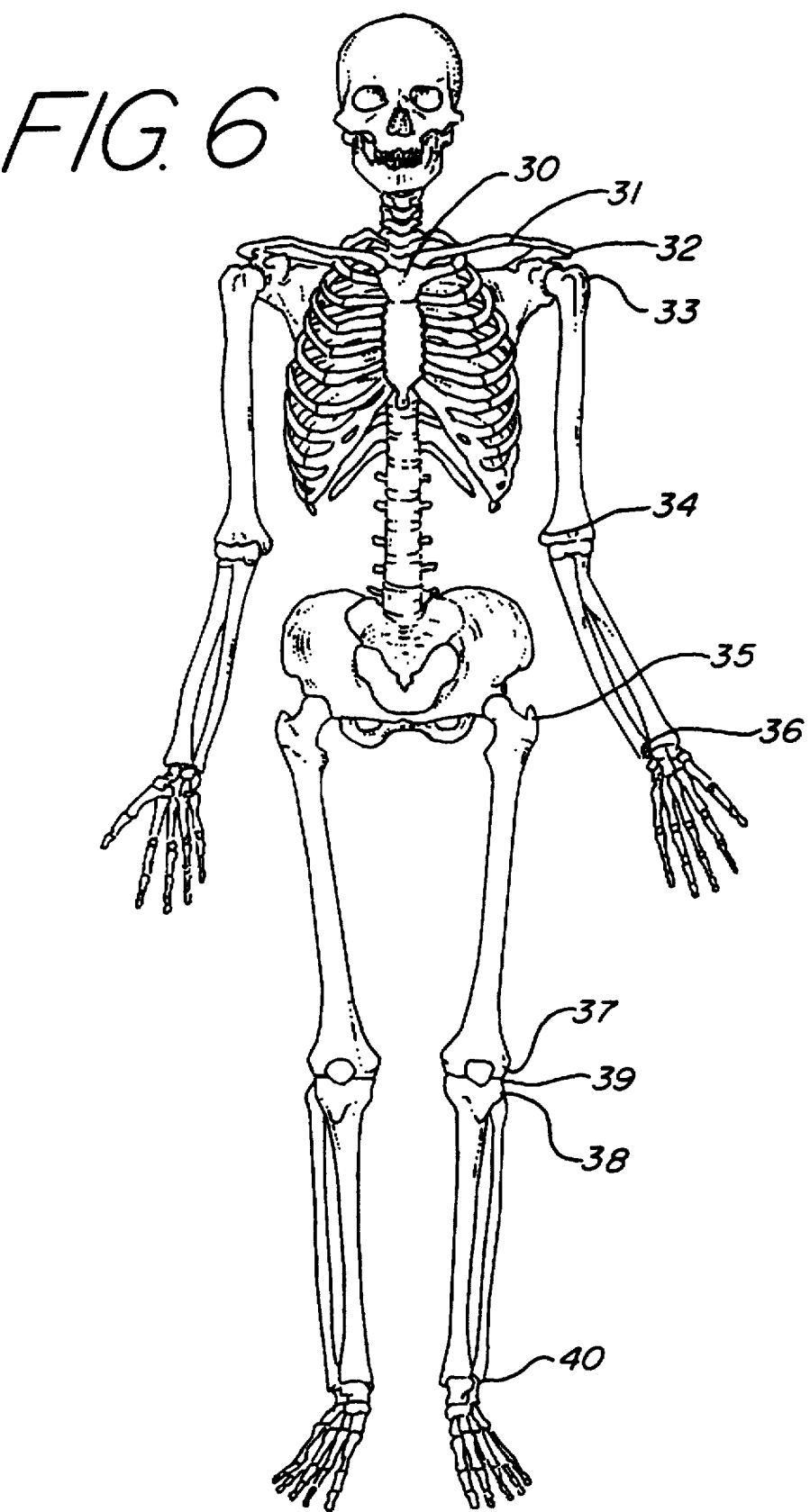

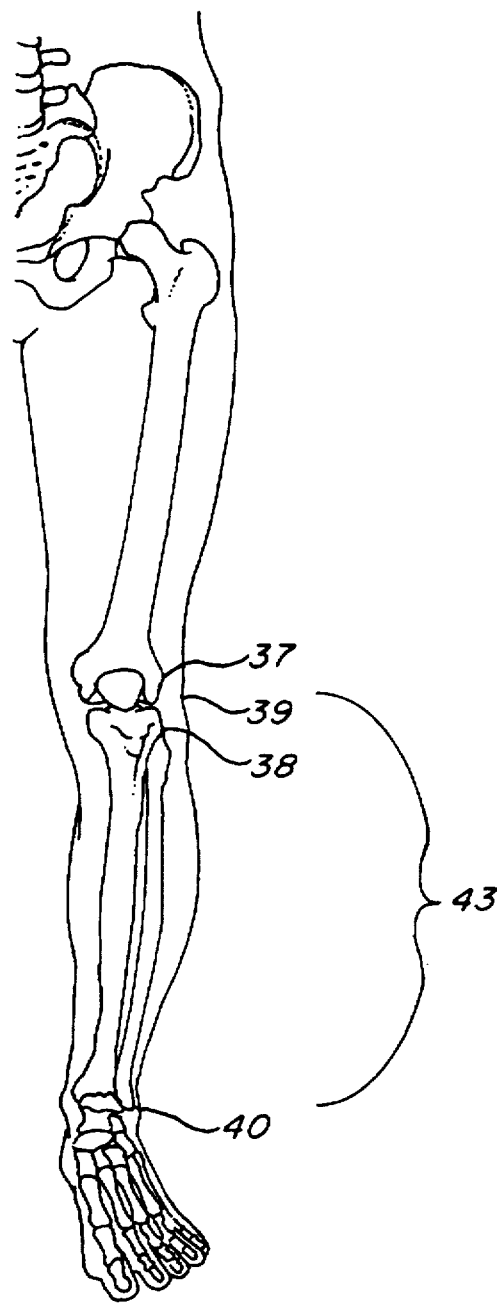
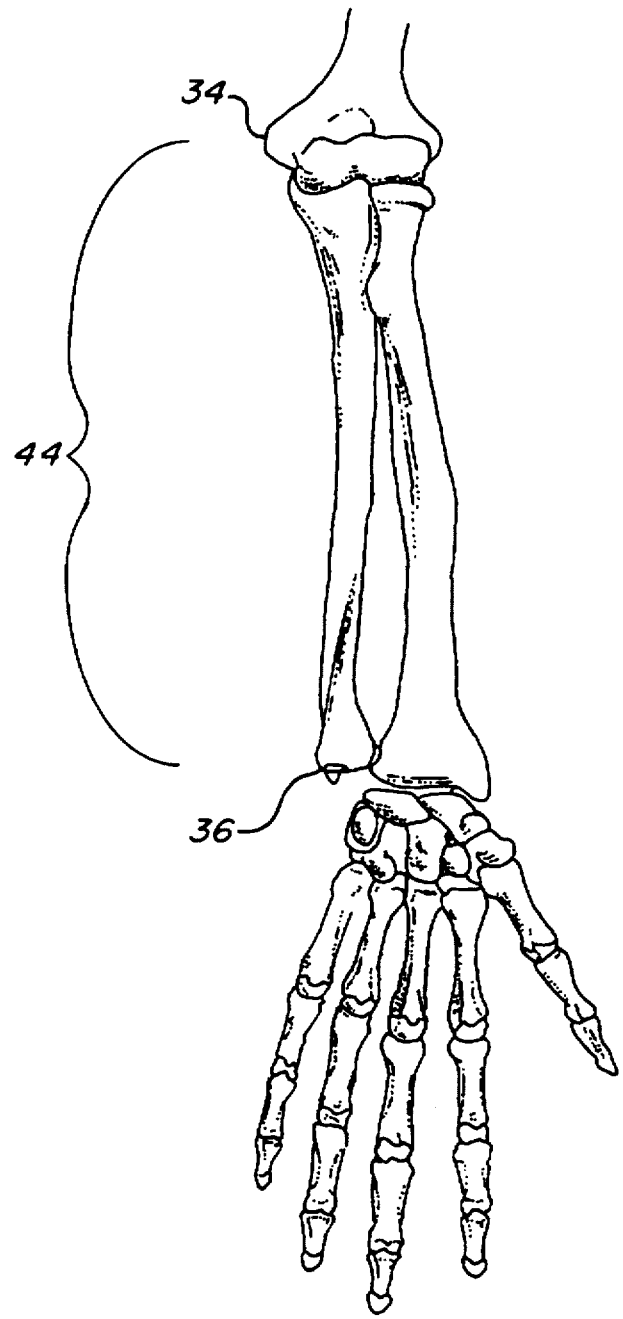
FIG. 9
FIG. 10

METHOD AND APPARATUS FOR MEASUREMENT OF POINTS ON THE HUMAN BODY

This application is a continuation-in-part of a previous application filed in the United States Patent and Trademark Office by inventors David R. Riley, Gerald D. Riley, and Gregory Holman on Sep. 2, 1994 entitled "Optimizer Measuring Unit" and assigned Ser. No. 08/300,485, now U.S. Pat. No. 5,586,558.

BACKGROUND OF THE INVENTION

The present invention is intended to assist in determining natural ranges of motion of any specific human individual. These anthropometric measurements are used in providing job safety for the work force and safety for individuals using a kinetic exercise program. The method and apparatus of the present invention obtains ten component variables from measurements of the individual. By using these variables, the ergonomic or health care professional can now fit the individual with the proper safety apparatus appropriate for that individual in a particular job task. In addition to determining the correct safety apparatus, data can be collected on certain characteristics of the human body to find trend and tendency patterns of certain ranges of motion that are at a higher risk of developing a repetitive motion injury while performing a specific job task. The present invention also addresses the problem of adjusting a work station to relieve any wasted motion that is out of that person's natural range of motion.

It is also a significant aspect of the present invention that the measurement data is taken in a systematic way, by measuring each person in the same way. Therefore, the data can be analyzed and compared over time to zero in on specific problem areas, and correct those areas even more quickly to reduce repetitive motion injuries. Using this systematic approach, individual height is no longer a factor, because the present invention provides for a beginning or point of origin from which all measuring data is collected. The point of origin is the top of the sternoclavicular joint or suprasternal notch of the human body. By making all measurements in relation to this standard point of origin, the height of the individual being measured is not a factor, which makes the use and processing of the data simpler.

SUMMARY OF THE INVENTION

The present invention is a method and apparatus for making measurements of points on the human body. The method of the present invention is a method of making measurements which relates all measurements to a standard point of origin on the human body. By this method, the measurements are standardized, variation in the height of the individual is reduced as a factor, and more consistent and useful data is obtained. The point of origin selected for the practice of the present invention is the top of the sternoclavicular joint or the suprasternal notch. This point is easily located and provides a reproducible and consistent set of measurements. One or more mathematical coordinate systems are selected having each coordinate system origin coinciding with the selected point of origin on the human body. Therefore, any measurement can be related to the single unique point of origin, the top of the sternoclavicular joint or suprasternal notch.

The present invention also provides for an apparatus for measurement of points on the human body as required by the method of the present invention. The apparatus is composed of a stand and a base plate. The apparatus has arms that extend from the stand to right and from the stand to left. The arms have a measuring apparatus attached to the end of each arm. The measuring apparatus attached to the arm to right is a vertical disc having one degree graduations etched on its surface in four segments totalling 360 degrees—two of the segments read from 0 to −90 degrees and two of the segments read from 0 to +90 degrees. Attached to this disc at the center point is a vertically oriented torso rule having graduations etched onto the rule in ¼ inch increments starting at 0 inches and reading through 30 inches. Mounted on the torso rule is a slide assembly constructed of square tubing which adjusts up and down vertically on the torso rule to measure torso lengths. Also attached to the vertical disc at the center point is a radial dial arm having ¼ inch graduations etched on the surface starting at 0 inches and running through 24 inches. The radial dial arm is used together with the vertical disc to make measurements radially with reference to the center of the vertical disc which is placed at the point of origin on the body of the individual being measured. Mounted on the radial dial arm is a slide assembly with a penlight. The slide assembly slides up and down the radial dial arm.

From the stand to left is an arm at the end of which is a horizontal half circle flat disc. The half circle disc has graduations in one degree increments from 0 degrees to 90 degrees and from 90 degrees to 0 degrees etched on the surface along the outer edge. The intersection of the 0 degree line and 90 degree line of the half circle disc defines an origin from which measurements are made. The origin of the half circle flat disc is also placed on the point of origin on the body of the individual being measured so that all measurements are made from the same reference point; i.e., the top of the sternoclavicular joint or suprasternal notch. Attached to the point of intersection is a dial arm which is used for pointing to the exact degree measurement.

Further objects and advantages of the present invention will be apparent from a consideration of the detailed description of the preferred embodiments in conjunction with the drawings which are described as follows.

BRIEF DESCRIPTION OF THE DRAWINGS

FIG. 2 is a top plan view of the measuring apparatus.

FIG. 5 is a perspective view of the horizontal half disc on the end of the left arm of the measuring apparatus.

FIG. 6 is a front elevation of a human skeleton.

FIG. 9 is a front elevation of the bone structure of a human left leg showing schematically the measurement of points on the lower leg.

FIG. 10 is front elevation of the bone structure of a human lower left arm with the palm of the hand held outward showing schematically the measurement of points on the lower arm.

DETAILED DESCRIPTION OF THE PREFERRED EMBODIMENTS

Figure 1:
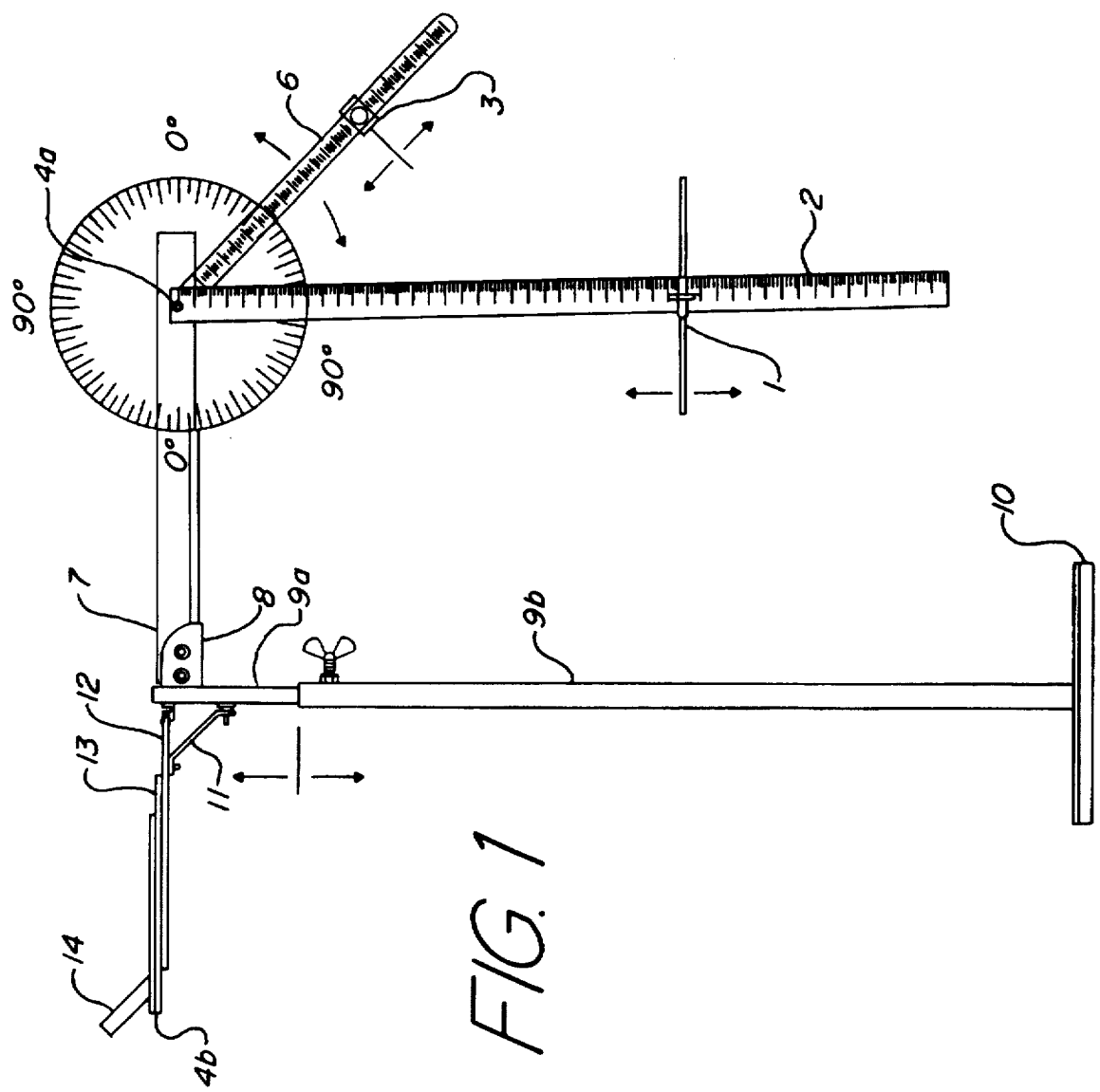
FIG. 1 is a front elevation view of the measuring apparatus of the present invention.
Figures 3, 11:
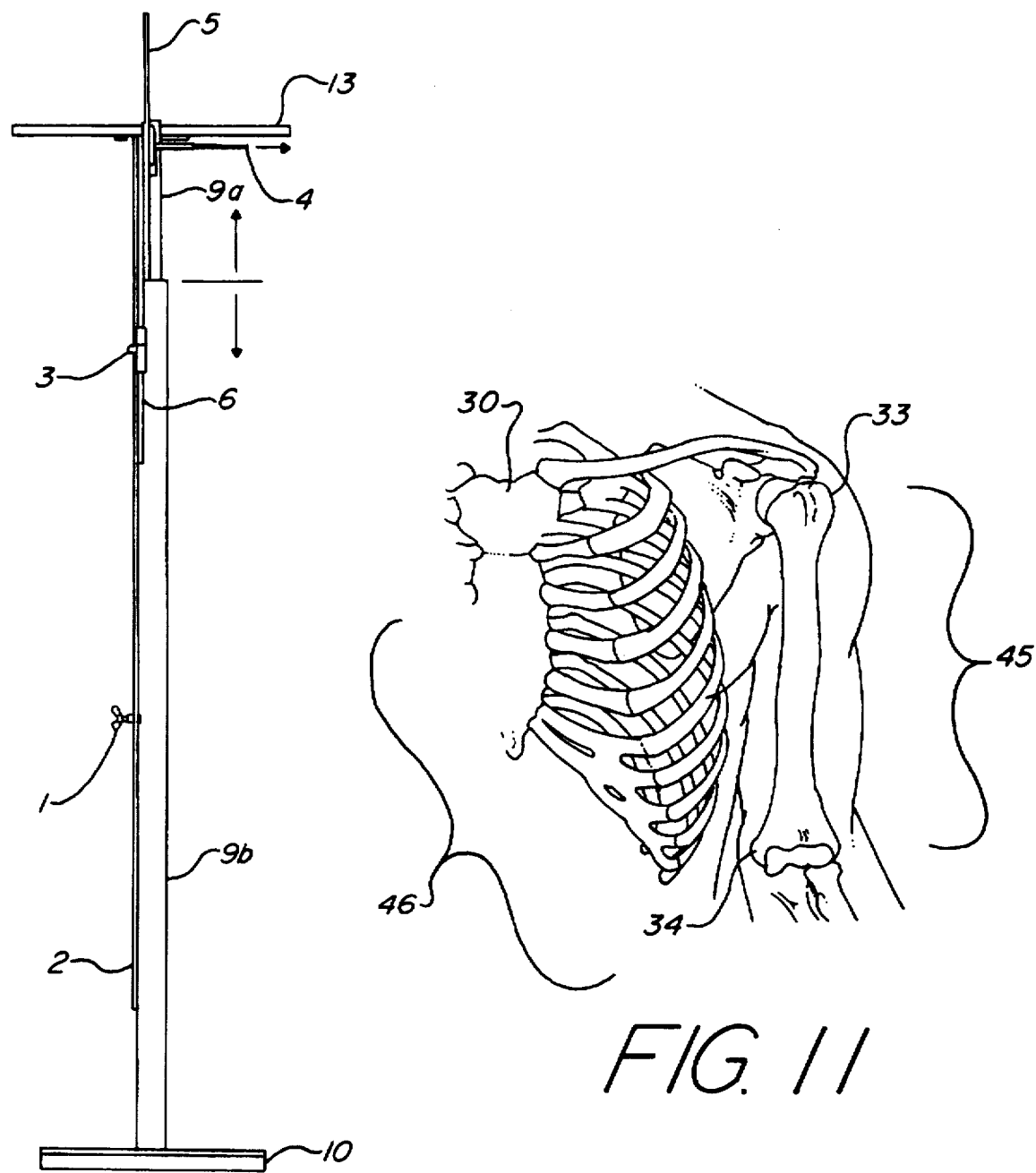
FIG. 3 is a right side elevation view of the measuring apparatus.
FIG. 11 is a partial front elevation of the human torso and upper left arm showing schematically the measurement of points of the upper arm.
Figures 4, 4A:
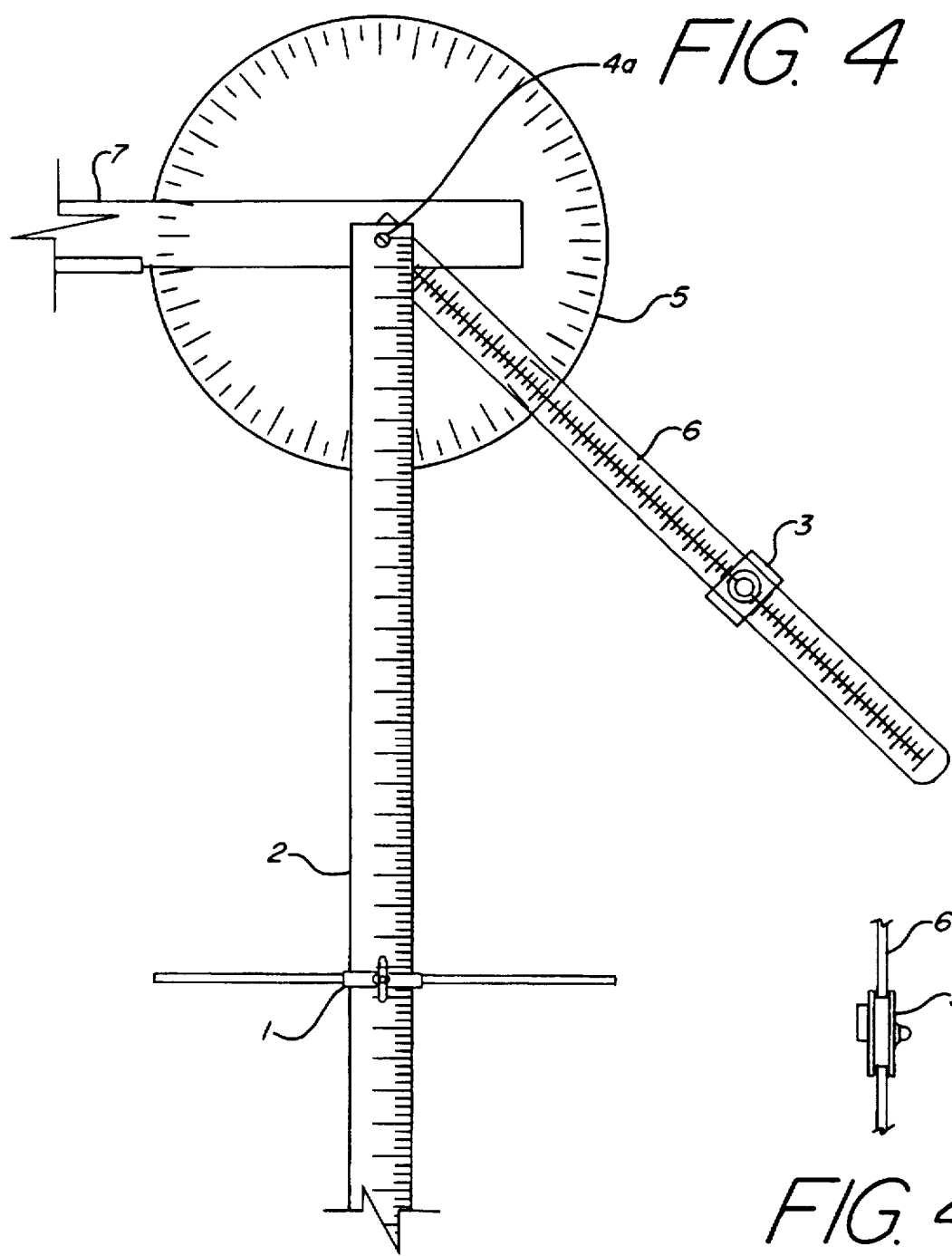
FIG. 4 is a partial detailed front elevation view of the right arm of the measuring apparatus.
FIG. 4A is a detailed side view of the slide on the radial dial arm.

The preferred embodiments of the present invention may now be described with reference to drawing FIGS. 1–5. The measuring apparatus of the present invention is comprises a stand 9a, 9b and a base plate 10. The stand 9a, 9b is preferably constructed of metal. The stand 9a, 9b when retracted is 4 feet in height and extends to 6 feet 8 inches in height. This is a sufficient range to accommodate most individuals, although the present invention is not limited to this particular range.

The measuring apparatus has a base plate 10 from which a vertical extending column 9b is supported. Column 9b is attached to base plate 10 by gusset welds. Inside column 9b is a vertical extending column tube 9a which extends out of column 9b for height adjustment of the measuring unit up and down on a vertical plane.

The stand 9a, 9b has arms 7, 12 that extend from the stand 9a, 9b to right and from stand 9a, 9b to left, respectively. The arms 7, 12 are preferably constructed of metal and are preferably 16 inches in length. At the top and to the right of tube 9a is bracket 8 which is secured to tube 9a. Bracket 8 extends out two inches and right support arm 7 is secured to bracket 8 at tube 9a.

The arms 7, 12 have a measuring assembly attached to the end of each arm 7, 12. Right support arm 7 extends out on a horizontal plane where disc 5 is mounted to right support arm 7 at center point 4a. Center point 4a may be extended out from the center of the disc 5 for ease in locating the standard point of origin on the human body as described more fully hereinafter. A zero degree line is established through center point 4a on a horizontal plane. A ninety degree line follows a straight line on a vertical plane through center point 4a. Both the zero degree line and the ninety degree line are etched on disc 5 as black graduations in one degree increments.

Attached to the disc 5 at the center point 4a is a torso rule 2, which is preferably thirty inches in length and two inches in width, having graduations etched onto its surface in ¼ inch increments starting at zero inches and reading through thirty inches.

Mounted on the torso rule 2 is a slide assembly 1, which is preferably constructed of metal and which is preferably twelve inches in total length having five inches to the left, five inches to the right and two inches on the rule 2 itself. The torso rule slide 1 is preferably a two inch square metal bracket which adjusts up and down vertically on the torso rule 2 to measure the length of the human torso. Rule slide 1 manually slides vertically on torso rule 2 for the purpose of obtaining accurate measurements of the human torso.

Also attached to the disc 5 at the center point 4a is a radial dial arm 6. The radial dial arm 6 is preferably made of plexiglass ⅛ inch thick and twenty inches long and having ¼ inch graduations etched on its surface starting at zero inches and running through twenty-four inches. Radial dial arm 6 rotates around center point 4a counterclockwise and clockwise. Mounted on the radial dial arm 6 is a slide 3 with a penlight assembly, which is preferably constructed of metal. The slide 3 slides up and down the radial dial arm 6 for accurate measurements in length and degrees of points on the upper extremities of the human body. Slide 3 slides on radial dial arm 6 over the etched graduations on radial dial arm 6. These graduations on radial dial arm 6 start at center point 4a at zero inches and run through the twenty four inch mark. It may be seen than that all points measured with the torso rule 2 or the radial dial arm 6 are made with respect to the same point of origin established by the center point 4a.

From the stand 9a, 9b to left is a left support arm 12, which is supported by support 11 attached to tube 9a. Left support arm 12 is preferably constructed of metal. Support 11 is secured to tube 9a and secured to left support arm 12 for support of left support arm 12. Left support arm 12 extends out as a support arm for half circle flat disc 13. At the end of the left support arm 12 is a horizontal half circle flat disc 13 mounted to the left support arm 12. This half circle flat disc 13 is preferably ⅛ inch thick and has a twenty-two inch radius with graduations in one degree increments from 0 degrees to 90 degrees and 90 to 0 degrees etched on its surface along the outer edge. Half circle flat disc 13 is a protractor preferably constructed of plexiglas with black graduations etched onto the surface in one degree increments. Half circle flat disc 13 is secured to left support arm 12 to keep half circle flat disc 13 in a fixed position. In the center of the half circle flat disc 13 in a straight line to the furthest edge is the 90 degree line. Half circle flat disc 13 has a zero degree line on a horizontal plane that runs flat across pivot point 4b as shown in FIG. 5. The zero line is on the left and right side of pivot point 4b, and the 90 degree line is directly in front of the zero line ninety degrees from zero line at pivot point 4b. At the center of the zero degree line where it intersects the 90 degree line is pivot point 4b. Pivot point 4b is also used to relate the measurements made with the half circle flat disc 13 to the reference point of origin on the body of the individual being measured as described more fully hereinafter. Attached to this pivot point 4b is a depth angle protractor dial arm 14 used for finding the degree angle of the clavicle of a human body on a horizontal plane. Dial arm 14 is a protractor dial preferably one inch wide and ten inches in length. Dial arm 14 lies flat on the top of half circle flat disc 13 and pivots about pivot point 4b in a half circle to pinpoint the different degree angles of the clavicle on the human body on a horizontal plane.

Figure 8:
FIG. 8 is a partial front elevation of a human skeleton and associated musculature of the the human torso.
Figure 7:
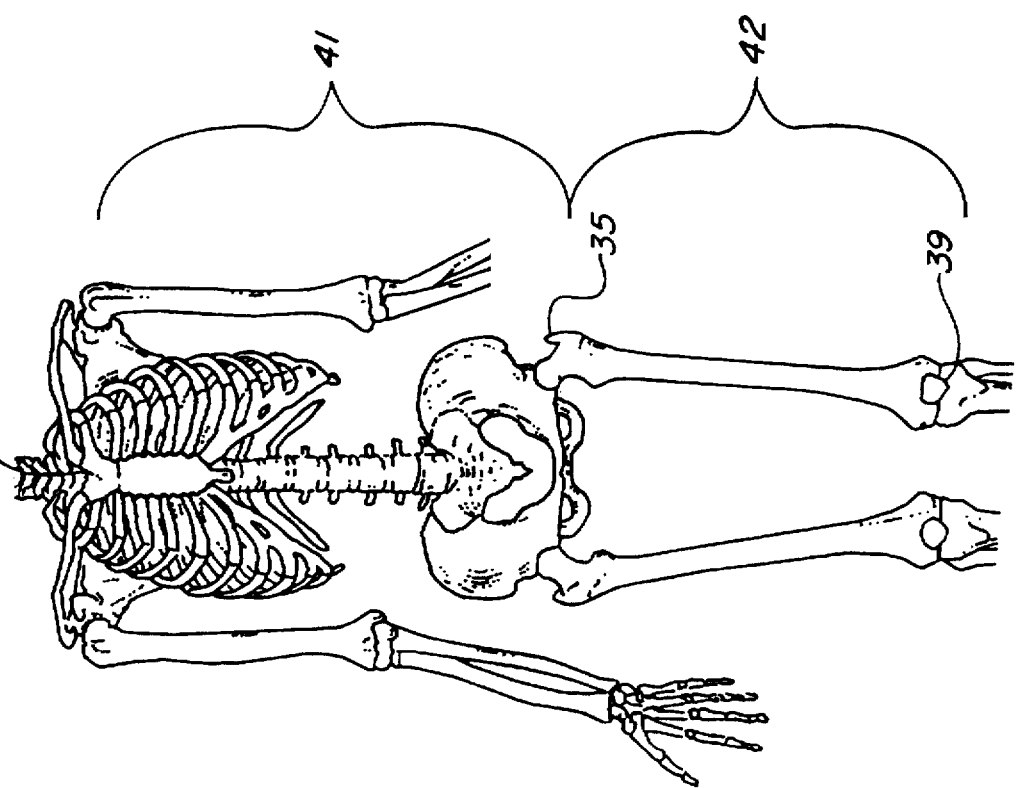
FIG. 7 is a partial front elevation of a human skelton showing schematically the measurement of points on the torso and upper leg.

The method of the present invention is described with reference to FIGS. 6–11. In finding these measurement points required by the present invention, the user must first locate the suprasternal notch at the top of the sternum, which is the point of origin 30 for all measurements. The user makes a mark at the top middle of the sternum. Palpating the clavicle moving toward the shoulder, the user locates the delto-pectoral triangle 31. Drawing a small diagonal line, the user continues to palpate along the clavicle to the acromion-clavicular joint 32 where a small mark is made.

After placing the individual's arm in an anatomical position palms out, the user palpates the shoulder to find the greater tubercle of the humerus 33 at the proximal end of the upper arm, and makes a small mark. The user then places a hand on the inside of the elbow, palpates the elbow and finds the medial epicondyle of the humerus 34, which is also marked. The mark made on the medial epicondyle of the humerus 34 is the point that is used to measure the radius and angle of the elbow from the point of origin 30.

Next, the user palpates the wrist to find the styloid process of the ulna 36 on the medial side of the wrist in anatomical position. A mark is made at the distal end of the styloid process of the ulna 36.

In order to find the hip landmark the user has the individual being measured to stand in a relaxed position facing the user while the user is in a seated position. As the individual lifts his leg out away from his body, the user looks for the crease in the hip. Place the right hand on the crease, the user palpates the crease while the individual being measured repeats the leg lift. The user feels for the top of the greater trochanter of the femur 35. This point is marked later for measurement.

The user has the individual bend at the knee slightly forward and palpates for the crease between the lateral condyle of the femur 37 and the condyle of the tibia 38. A mark is made at a point 39 between those two points.

A mark is made in the center of the lateral malleolus 40 of the ankle.

This locates all the measurement landmarks for the measuring procedure using the apparatus of the present invention.

Each arm of the measuring apparatus may be leveled as needed. The individual being measured is placed behind the radial dial disc 5 approximately three inches away in an anatomical position with arms relaxed at side. The height of the stand 9a, 9b is adjusted until the center point 4a is at the height of the suprasternal notch or point of origin 30. A point of origin marker may be used to ensure accurate adjustment of the stand 9a, 9b to the point of origin 30 which is the mark on the suprasternal notch previously made. It is desirable that the individual not rotate his shoulders and keep square to the measurement apparatus while the measurements are being made.

In order to take the first measurement, the user rotates the radial dial arm 6 in an upward motion toward the shoulder. The user than slides the radial dial arm slide 3 out to the mark made on the acromion-clavicular joint 32 and takes the measurement of the clavicle 47 (length and angle from point of origin 30).

The next measurement to be taken is the elbow radius and angle 46. With the individual being measured in the same anatomical position with arms relaxed at side as before, the user rotates the radial dial arm 6 down to the elbow (medial epicondyle of the humerus 34) and measures the elbow radius and angle 46 from the point of origin 30.

The next measurements are made with the torso rule 2 and torso rule slide 1. The hip joint is located by the crease of the hip as described above. When the hip joint location is determined, the individual is realigned behind the measurement apparatus with the point of origin 30 at the center point 4a. The user adjusts the torso slide 1 to the marked point on the hip joint (greater trochanter of the femur 35) to obtain the length of the torso 41 vertically from the point of origin 30.

Upon completion of the torso measurement procedure, the user measures the length of the upper leg 42 using the same procedure as with the torso rule 2 and slide 1 by measuring from the point on the greater trochanter 35 to the point 39 on knee marked earlier between the lateral condyle of the femur 37 and the lateral condyle of the tibia 38. The torso length 41 is measured vertically from the suprasternal notch or point of origin 30 to the crease in the hip 35 already established. The upper leg measurement 42 is also measured in inches.

The next measurement to be taken is the lower leg length 43. This measurement is desirably taken with calipers of the type known in the art rather than with the measuring apparatus of the present invention. The user places the pointer of the calipers on the lateral malleolus 40 (ankle) that has been premarked. The user then slides the caliper to the premarked point of the knee 39 to take the measurement.

The next measurement to be taken is the clavicle depth angle 47. The individual being measured changes to the left arm 12 of the measuring apparatus in front of the half circle flat disc 13, which is a depth angle protractor. The individual is placed so that the pivot point 4b in the center of the protractor 13 is on the suprasternal notch or point of origin 30 that has been premarked. It is desirable that the individual does not rotate his shoulders while the measurement is being made. The clavicle depth angle 47 is found by locating the delto-pectoral triangle 31 as described previously. The clavicle depth angle 47 is taken in degrees using the depth angle protractor dial arm 14.

The last two measurements to be taken are the upper arm 45 and lower arm 44 length measurements. These measurements are taken using calipers as described previously. The upper arm measurement 45 is taken from the greater tubercule of the humerus 33 to the medial epicondyle of the humerus 34. The lower arm measurement 44 is taken from the medial epicondyle of the humerus 34 to the styloid process of the ulna 36.

The present invention has been described with respect to certain preferred and alternative embodiments which are considered exemplary only and not limiting to the full scope of the invention as set forth in the appended claims.

The measuring apparatus of the present invention measures degree angle and anthropometric linear measurements of the skeletal structure of the human body. The individual stands behind the machine with the top of the sternoclavicular joint or suprasternal notch 30 at point 4a or 4b. Because every individual is measured from the same beginning point, or point of origin 30, a study can be done according to the data collected. From here 10 component variables are taken with the measuring unit. These variables are entered into a computer data base for calculation. This allows an infield study of individual workers at a work station or exercise on a resistance training program and or undergoing medical treatment for biomechanical correction. Studying repetitive motion injuries in the work force is one example (non-surgical). By measuring bone lengths and degree angles of a human body we have found that certain characteristics or trends can be found by this systematic measuring procedure. For example we have found that clients with equal bone lengths in upper legs (femur) and torso length, plus a shorter length in lower leg (tibia) have a 0 degree torso deflection range and these individuals experience chronic low back pain. This means these individuals are at extremely high risk of experiencing a lower lumbar injury that can injure them greatly. Nine graphs are generated so that reaching, bending, twisting, pressing, pulling, and sitting can be broken down into exact biomechanical movements for a specific muscle range group.

All measurements are taken with the individual standing behind the measuring unit in a relaxed posture. Every individual is measured from the same point of origin. This gives the user a systematic way of taking measurements on every individual in the same manner.

The point of origin 30 for all measurements is the top of the sternoclavicular joint, or suprasternal notch, of the human body. The fixed plexiglass disc 5 has its center point 4a coincident with the point of origin 30. The radial dial arm 6 pivots about the same center point 4a and therefore measures degree angles from the center point 4a. Slide 3 slides along the radial dial arm 6 and measures lengths from the center point 4a. In this manner any point on the human body may be measured with reference to the center point 4a in polar coordinates of degrees and lengths from the center point 4a. The torso rule 2 is also related to the same point of origin 30 through being affixed at the center point 4a. The rule slide 1 slides up and down along the torso rule 2 and therefore measures the length of the human torso from the top of the sternum; i.e. the top of the sternoclavicular joint or suprasternal notch, to the hip socket with reference to the same point of origin 30. Finally, the depth angle protractor comprising the half circle flat disc 13 and dial arm 14 together measure the degree angle of the clavicle bone on a horizontal plane of the human body as described more fully below.

What is claimed is:

1. In a measuring device used for determining the location of points on the skeletal system of a human body for purposes of determining natural ranges of motion of any specific individual as used in ergonomics, fitness and job safety, at least one measuring means having an origin defining a coordinate system by which the points on the skeletal system of the human body are measured, said origin being adapted to being placed coincident with a point of origin on the human body, said point of origin being a bony landmark on the skeletal system of the human body, whereby the points on the skeletal system are determined in relation to said point of origin, and further wherein said landmark on the skeletal system of the human body is the suprasternal notch of the human body.

2. A method of measuring points on the skeletal system of a human body, comprising the steps of:
   (a) establishing a point of origin which is a bony landmark on the skeletal system of the human body, wherein said point of origin is the suprasternal notch of the human body, and
   (b) measuring points on the skeletal system of the human body with reference to said point of origin.

3. The method of claim 2 wherein step (b) comprises measuring the length of the torso of the human body, the length of the upper leg of the human body, the Length of the lower leg of the human body, the length of the upper arm of the human body, the length of the lower arm of the human body, the length and angle on a horizontal plane from said point of origin of the clavicle of the human body, and the length and angle on a vertical plane from said point of origin of the elbow of the human body.

4. The method of claim 3 wherein said length of the torso is measured vertically from said point of origin to the greater trochanter of the femur of the human body, said length of the upper leg is measured vertically from the greater trochanter of the femur to a knee point midway between the lateral condyle of the femur and the lateral condyle of the tibia of the human body, the length of the lower leg is measured vertically from said knee point to the lateral malleolus of the fibula, the length of the upper arm is measured vertically from the greater tubercule of the humerus to the medial epicondyle of the humerus, the length of the lower arm is measured from the medial epicondyle of the humerus to the styloid process of the ulna, the length and angle of the clavicle is measured from said point of origin to the acromion-clavicular joint, and the length and angle of the elbow is measured from said point of origin to the medial epicondyle of the humerus.

5. The method of claim 4, comprising the additional step subsequent to step (b) of analyzing said measured points on the skeletal system of the human body to predict the biomechanical performance of the human body.

* * * * *